United States Patent
Mao et al.

(10) Patent No.: US 10,119,202 B2
(45) Date of Patent: Nov. 6, 2018

(54) METHOD FOR PREPARING ELECTRO-MECHANICALLY STRETCHED HYDROGEL MICRO FIBERS

(71) Applicant: THE JOHNS HOPKINS UNIVERSITY, Baltimore, MD (US)

(72) Inventors: Hai-Quan Mao, Baltimore, MD (US); Shuming Zhang, Lehigh Acres, FL (US); Xi Liu, Suzhou (CN); Brian Patrick Ginn, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 774 days.

(21) Appl. No.: 14/398,072

(22) PCT Filed: Apr. 30, 2013

(86) PCT No.: PCT/US2013/038805
§ 371 (c)(1),
(2) Date: Oct. 30, 2014

(87) PCT Pub. No.: WO2013/165975
PCT Pub. Date: Nov. 7, 2013

(65) Prior Publication Data
US 2015/0118195 A1    Apr. 30, 2015

Related U.S. Application Data

(66) Substitute for application No. 61/665,498, filed on Jun. 28, 2012.
(Continued)

(51) Int. Cl.
*D01D 5/34* (2006.01)
*D01D 7/00* (2006.01)
(Continued)

(52) U.S. Cl.
CPC .............. *D01D 5/003* (2013.01); *A61L 27/48* (2013.01); *A61L 27/52* (2013.01); *A61L 27/54* (2013.01);
(Continued)

(58) Field of Classification Search
CPC ...... D01D 5/0046; D01D 5/0076; D01D 5/06; D01D 5/34; D01D 7/00; D01D 10/02;
(Continued)

(56) References Cited

U.S. PATENT DOCUMENTS 7,086,846 B2   8/2006 Kleinmeyer
8,012,399 B2   9/2011 Gee
(Continued)

FOREIGN PATENT DOCUMENTS

EP    1994949 A1    11/2008
WO    2004080681 A1    9/2004

OTHER PUBLICATIONS

International Search Report dated Aug. 12, 2013 for PCT/US2013/038805.
(Continued)

*Primary Examiner* — Leo B Tentoni
(74) *Attorney, Agent, or Firm* — Casimir Jones, S.C.; Jeffrey W. Childers

(57) ABSTRACT

The presently disclosed subject matter provides a scalable and electrostretching approach for generating microfibers exhibiting uniaxial alignment from polymer solutions. Such microfibers can be generated from a variety of natural polymers or synthetic polymers. The hydrogel microfibers can be used for controlled release of bioactive agents. The internal uniaxial alignment exhibited by the presently disclosed fibers provides improved mechanical properties to microfibers, contact guidance cues and induces alignment for cells seeded on or within the microfibers.

25 Claims, 6 Drawing Sheets

Related U.S. Application Data

(60) Provisional application No. 61/640,057, filed on Apr. 30, 2012.

(51) Int. Cl.

| | | |
|---|---|---|
| *D01D 10/02* | (2006.01) | |
| *D01F 1/10* | (2006.01) | |
| *D01F 4/00* | (2006.01) | |
| *D01F 6/14* | (2006.01) | |
| *D01F 6/16* | (2006.01) | |
| *D01F 6/50* | (2006.01) | |
| *D01F 6/52* | (2006.01) | |
| *D01F 6/60* | (2006.01) | |
| *D01F 6/62* | (2006.01) | |
| *D01F 8/02* | (2006.01) | |
| *D01F 8/10* | (2006.01) | |
| *D01F 8/12* | (2006.01) | |
| *D01F 8/14* | (2006.01) | |
| *D01F 11/02* | (2006.01) | |
| *D01F 11/06* | (2006.01) | |
| *D01D 5/00* | (2006.01) | |
| *D06M 10/00* | (2006.01) | |
| *D01D 5/06* | (2006.01) | |
| *D01D 5/12* | (2006.01) | |
| *A61L 27/48* | (2006.01) | |
| *A61L 27/52* | (2006.01) | |
| *A61L 27/54* | (2006.01) | |
| *D01F 2/00* | (2006.01) | |

(52) U.S. Cl.
 CPC ......... *D01D 5/0046* (2013.01); *D01D 5/0076* (2013.01); *D01D 5/06* (2013.01); *D01D 5/12* (2013.01); *D01F 2/00* (2013.01); *D06M 10/001* (2013.01); *A61L 2430/00* (2013.01); *D10B 2201/01* (2013.01); *D10B 2211/01* (2013.01); *Y10T 428/298* (2015.01); *Y10T 428/2967* (2015.01)

(58) Field of Classification Search
 CPC ..... D01F 1/10; D01F 4/00; D01F 6/14; D01F 6/16; D01F 6/50; D01F 6/52; D01F 6/60; D01F 6/62; D01F 8/02; D01F 8/10; D01F 8/12; D01F 8/14; D01F 11/02; D01F 11/06; D06M 10/001
 USPC ........ 264/10, 103, 172.15, 211.12, 234, 236, 264/464, 465, 466, 484, 494
 See application file for complete search history.

(56) References Cited

U.S. PATENT DOCUMENTS

| | | | |
|---|---|---|---|
| 8,062,567 B2 | 11/2011 | Watanabe et al. | |
| 2002/0133229 A1* | 9/2002 | Laurencin | A61F 2/08 623/13.17 |
| 2008/0241538 A1 | 10/2008 | Lee et al. | |
| 2008/0296808 A1 | 12/2008 | Joo et al. | |
| 2010/0001438 A1 | 1/2010 | Kishimoto | |
| 2010/0113857 A1* | 5/2010 | Ramakrishna | D01F 1/10 588/299 |
| 2011/0155956 A1* | 6/2011 | Ashraf | B82Y 30/00 264/465 X |
| 2011/0180972 A1 | 7/2011 | Lee et al. | |
| 2011/0201242 A1* | 8/2011 | Hur | D01F 1/10 442/181 |
| 2011/0238178 A1* | 9/2011 | Downes | A61L 27/18 264/465 X |
| 2014/0377213 A1* | 12/2014 | Hong | A61L 27/58 424/78.38 |
| 2015/0045454 A1* | 2/2015 | Kong | D01F 1/10 264/465 X |

OTHER PUBLICATIONS

Wall, B.D., et al, Aligned macroscopic domains of optoelectronic nanostructures prepared via shear-flow assembly of peptide hydrogels, Adv. Mater., 23, 5009-5014 (2011).

Bellan, L. M. and Craighead, H. G. Molecular orientation in individual electrospun nanofibers measured via polarized Raman spectroscopy. Polymer 49, 3125-3129 (2008).

Yang, Y., et al, Monitoring the effect of magnetically aligned collagen scaffolds on tendon tissue engineering by PSOCT, Proc. SPIE 7179, Optics in Tissue Engineering and Regenerative Medicine III, 717903 (Feb. 12, 2009).

Tonsomboon, K., and Oyen, M.L., Composite electrospun gelatin fiber-alginate gel scaffolds for mechanically robust tissue engineered cornea, J. Mechanical Behavior of Biomedical Materials, 21:185-94 (2013).

Guo, C. and Kaufman, L.J., Flow and magnetic field induced collagen alignment, Biomaterials 28: 1105-1 114 (2007).

Kaneko, T., et al, Mechanically drawn hydrogels uniaxially orient hydroxyapatite crystals and cell extension, Chem. Mater. 5596-5601 (2004).

Zang, X. H., Kim, K., Fang, D., Ran, S., Hsiao, B.S., and Chu, B. Structure and process relationship of electrospun bioabsorbable nanofiber membranes. Polymer 43, 4403-4412 (2002).

Yang, F., Murugan, R., Wang, S. and Ramakrishna, S. Electrospinning of nano/micro scale poly(L-lactic acid) aligned fibers and their potential in neural tissue engineering. Biomaterials 26, 2603-2610 (2005).

Williams, C. G., Kim, T.K., Taboas, A., Malik, A., Manson, P. and Elisseeff, J. In vitro chondrogenesis of bone marrow-derived mesenchymal stem cells in a photopolymerizing hydrogel. Tissue Engineering 9, 679-688 (2003).

Shu, X. Z., Liu, Y. C, Palumbo, F. S., Lu, Y. and Prestwich, G. D. In situ crosslinkable hyaluronan hydrogels for tissue engineering. Biomaterials 25, 1339-1348 (2004).

Seliktar, D. Designing Cell-Compatible Hydrogels for Biomedical Applications, Science 336, 1124-1128 (2012).

Reneker, D. H., Yarin, A. L., Fong, H. and Koombhongse, S. Bending instability of electrically charged liquid jets of polymer solutions in electrospinning. J. Appl. Phys. 87, 4531-4547 (2000).

Potter, K., Balcom, B. J., Carpenter, T. A. and Hall, L. D. The gelation of sodium alginate with calcium-ions studied by magnetic-resonance-imaging (MRI). Carbohyd Res 257, 1 17-126 (1994).

Lim, S. H. and Mao, H. Q. Electrospun scaffolds for stem cell engineering. Advanced Drug Delivery Reviews 61, 1084-1096 (2009).

Larson, R. G. and Mead, D. W. The Ericksen Number and Deborah Number cascades in sheared polymeric nematics. Liq. Cryst. 15, 151-169 (199).

Kang, E., Jeong, G.S., Choi, Y.Y., Lee, K.H., Khademhosseini, A., and Lee,S.-H. Digitally tunable physicochemical coding of material composition and topography in continuous microfibres. Nature Materials 10, 877-883 (2011).

Kakade, M. V., Givens, S., Gardner, K., Lee, K.H., Chase, D.B., and Rabolt, J.F. Electric field induced orientation of polymer chains in macroscopically aligned electrospun polymer nanofibers. Journal of the American Chemical Society 129, 2777-2782 (2007).

Ji, Y., Ghosh, K., Shu, X.Z., Li, B., Sokolov, J.C., Prestwich, G.D., Clark, R.A.F., and Rafailovich, M.H. Electrospun three-dimensional hyaluronic acid nanofibrous scaffolds. Biomaterials 27, 3782-3792 (2006).

Ji, Y., Ghosh, K., Li, B., Sokolov, J.C., Clark, R.A.F., and Rafailovich, M.H. Dual-syringe reactive electrospinning of cross-linked hyaluronic acid hydrogel nanofibers for tissue engineering applications. Macromol Biosci 6, 81 1-817 (2006).

Inai, R., Kotaki, M. and Ramakrishna, S. Structure and properties of electrospun PLLA single nanofibres. Nanotechnology 16, 208-213 (2005).

Grasman, J. M., Page, R. L., Dominko, T. and Pins, G. D. Crosslinking strategies facilitate tunable structural properties of fibrin microthreads. Acta Biomaterialia 8, 4020-4030 (2012).

(56) References Cited

OTHER PUBLICATIONS

Fennessey, S. F. and Farris, R. J. Fabrication of aligned and molecularly oriented electrospun polyacrylonitrile nanofibers and the mechanical behavior of their twisted yarns. Polymer 45, 4217-4225 (2004).

Discher, D. E., Janmey, P. and Wang, Y. L. Tissue cells feel and respond to the stiffness of their substrate. Science 310, 1 139-1143 (2005).

Cornwell, K. G, and Pins, G. D. Discrete crosslinked fibrin microthread scaffolds for tissue regeneration. Journal of Biomedical Materials Research Part A 82A, 104-1 12 (2007).

Catalani, L. H., Collins, G. and Jaffe, M. Evidence for molecular orientation and residual charge in the electrospinning of poly(butylene terephthalate) nanofibers. Macromolecules 40, 1693-1697 (2007).

Burdick, J. A. and Anseth, K. S. Photoencapsulation of osteoblasts in injectable RGD-modified PEG hydrogels for bone tissue engineering, Biomaterials 23, 4315-4323 (2002).

Pant, H. et al. (2011). Fabrication of polymeric microfibers containing rice-like oligomeric hydrogel nanoparticles on their surface: A novel strategy in the electrospinning process. Materials Letters, 65(10), 1441-1444.

Lai, C., et al (2011). Investigation of postspinning stretching process on morphological, structural, and mechanical properties of electrospun polyacrylonitrile copolymer nanofibers. Polymer, 52(2), 519-528.

* cited by examiner

METHOD FOR PREPARING ELECTRO-MECHANICALLY STRETCHED HYDROGEL MICRO FIBERS

CROSS-REFERENCE TO RELATED APPLICATIONS

This application is a 35 U.S.C. § 371 U.S. national phase entry of International Application No. PCT/US2013/038805 having an international filing date of Apr. 30, 2013, which claims the benefit of U. S. Provisional Application Nos. 61/640,057, filed Apr. 30, 2012, and 61/665,498, filed Jun. 28, 2012; each of which is incorporated herein by reference in its entirety.

FEDERALLY SPONSORED RESEARCH OR DEVELOPMENT

This invention was made with government support under DMR-0748340 awarded by the National Science Foundation. The government has certain rights in the invention.

BACKGROUND

Hydrogels have been widely investigated for a variety of biomedical applications, particularly as scaffolds offering a 3-dimensional (3D) microenvironment for tissue regeneration. Hydrogels have been used for 3D cell culture and tissue regeneration because of their high water content resembling the aqueous microenvironment of the natural extracellular matrix (Seliktar, 2012) and tunable biochemical and physicochemical properties (Burdick and Anseth, 2002; Williams et al., 2003; Silva et al., 2004). While many properties of natural hydrogel matrices are modifiable, their inherent isotropic structure limits the control over cellular organization that is critical to restore tissue function.

Previous studies have primarily focused on exploring the mechanical and biochemical versatility of hydrogels and elucidating their impact on cellular activities (Engler et al., 2006; Discher et al., 2005; Lutolf et al., 2003; Dalsin et al., 2003; Martino et al., 2009). A lack of methodologies exists, however, for engineering anisotropic topographical cues in hydrogels to control the 3D spatial patterns of encapsulated cells. As a result, controlling topographically induced cell alignment and migration has not been readily achieved for hydrogel matrices, even though such cellular manipulation on 2D substrates has been shown to be important in controlling cell organization, tissue microarchitecture, and biological function (Yang et al., 2005; Bettinger et al., 2009; Chew et al., 2008; Aubin et al., 2010).

Recently, Kang et al. reported a microfluidic-based alginate hydrogel microfiber with a surface alignment feature produced by solution extrusion through a grooved round channel, and demonstrated guided neurite outgrowth for neurons cultured on the surface of the microfibers (Kang et al., 2011). This alignment cue, however, is only confined to the surface of the microfibers. Zhang et al. have generated peptide nanofiber hydrogels with long range nanofiber alignment through heat-assisted self-assembly of amphiphilic peptide molecules and mechanical shear (Zhang et al., 2010). Although the resulting aligned nanofiber "noodles" effectively induced cellular alignment in 3D, this method is only applicable to specific peptide materials.

On the other hand, cellular alignment mediated by 2D electrospun nanofiber matrices has been shown to effectively promote stem cell differentiation and cellular functions (Lim and Mao, 2009; Ji et al., 2006). Although dispersing solid polymer nanofibers into the hydrogel matrix has been used to generate a composite scaffold (Coburn et al., 2011), controlling alignment of the nanofibers inside a hydrogel matrix is challenging.

SUMMARY

In some aspects, the presently disclosed subject matter provides a method for preparing a microfiber having a uniaxial alignment, the method comprising: (a) providing at least one starting solution comprising one or more polymers; (b) applying an electrical potential to the at least one starting solution sufficient to initiate a jet stream of polymer solution; and (c) mechanically stretching the jet stream of polymer solution during or after collecting the jet stream of polymer solution in a collection bath comprising a stabilizing solution, wherein the collection bath is positioned at a separation distance such that the jet stream of polymer solution is collected before it is accelerated by an electrical field created by the applied electrical potential.

In other aspects, the presently disclosed subject matter provides a microfiber prepared by the presently disclosed methods.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
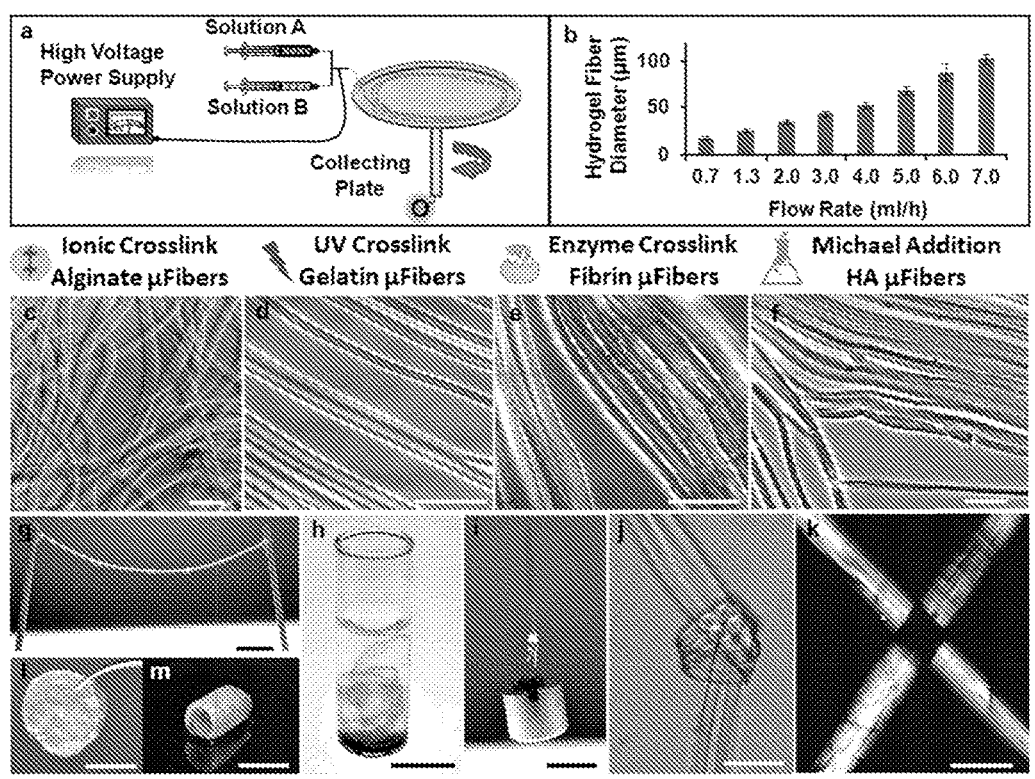
Figure 5:
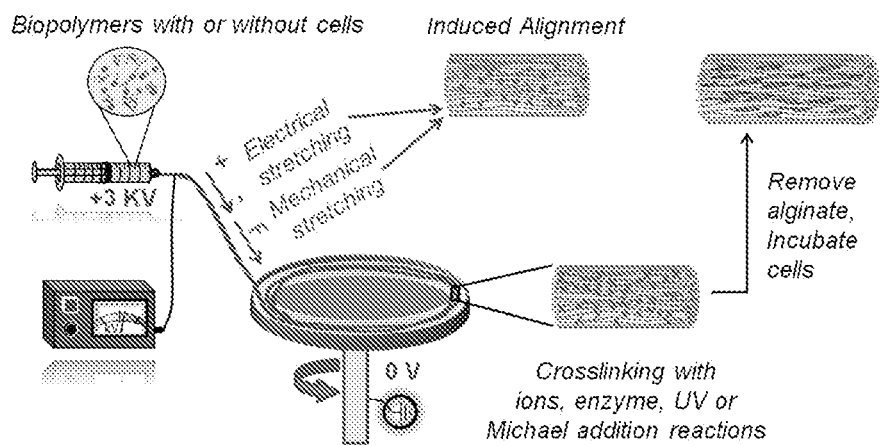
Figure 6:
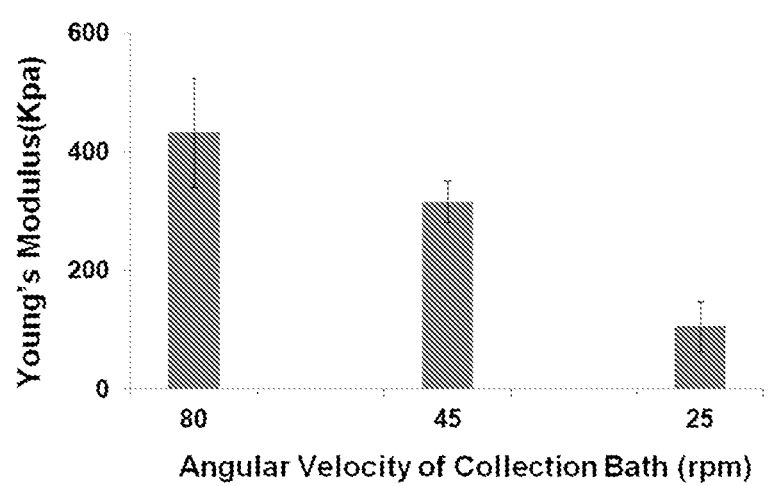

Having thus described the presently disclosed subject matter in general terms, reference will now be made to the accompanying Figures, which are not necessarily drawn to scale, and wherein:

FIGS. 1a-1m show the electrostretching setup and features of the presently disclosed hydrogel microfibers: (a) illustration of a representative spinning setup for electrostretching; (b) effect of alginate solution feeding rate on the diameter of the hydrogel microfibers. Alginate hydrogel microfibers with an average of 17-116 μm were prepared with a solution containing 2% sodium alginate and 0.2% PEG fed at a flow rate ranging from 0.7-7.0 ml/h. Bars represent mean±s.d. (n=3); (c-f) demonstrate that various crosslinking mechanisms have been employed to crosslink alginate, gelatin, fibrin, and hyaluronic acid hydrogel microfibers. The crosslinking of the fibers was initiated with a fast calcium gelation of alginate, followed by additional crosslinking of the second component polymer with UV-initiated, enzymatic, or the Michael addition reaction for methylated gelatin, fibrin and hyaluronic acid, respectively; (g) using this method, hydrogel microfibers of any desired length can be prepared; (h) when dispersed in water, alginate hydrogel fibers formed a loose network of hydrogel fibers. Trypan blue was used to stain the fibers and enhance observation; (i) a 10-g metal weight was lifted with an alginate hydrogel microfiber bundle; (j) a micro-knot was made with two alginate hydrogel microfibers; (k) under a cross polarized light microscope, light extinction was observed at the crossover point of two hydrogel microfiber bundles, indicating uniform alignment in both fibers; (l-m) beyond microfiber bundles, these hydrogel microfibers also can be fabricated into other forms like fibrous films (l) and self-supporting hydrogel tubes (m). Scale bars represent 100 μm in (c-f), 1 cm in (g-i) and (l-m), 50 μm in (j), and 1 mm (k);

FIGS. 2a-2i show SEM micrographs of hydrogel fibers prepared with simple extrusion and electrostretching. (a-c) Fibrin (a), gelatin (b) and HA (c) hydrogels prepared by simple extrusion or mixing consist of randomly oriented nanofiber network. (d-f) Electrostretched fibrin (d), gelatin (e) and HA (f) hydrogel fibers showing preferential alignment. Arrows indicate the orientation of the microfiber longitudinal axis. (g-i) Fibrin (g), gelatin (h) and HA (i) hydrogel fibers following stretching and dehydration in air forming fiber bundles. Both fibrin and gelatin fibers preserved surface texture and grooves. Samples in (a-f) were prepared by the critical point drying technique; and samples in (g-i) were stretched and dried in air. Scale bars represent 1 µm in (a-b) and (d-e), 2 µm in (c) and (f), 20 µm in (g-h), and 40 µm in (i);

FIGS. 3a-3g show X-ray scattering diffraction patterns and tensile moduli of hydrogel fibers in dry and wet states. (a-b) Small angle X-ray scattering (SAXS) patterns of the dry (a) and wet (b) calcium alginate hydrogel fibers confirming an alignment axis along the microfiber orientation indicated by the arrows. (c) SAXS pattern of alginate hydrogel prepared by hand extrusion suggesting an isotropic structure. (d) Wide angle x-ray scattering pattern of the dry alginate microfibers confirming the polymer chain alignment along the fiber axis as indicated by the arrow. (e-g) Tensile moduli of alginate (AG), fibrin (FN), gelatin (GT) and hyaluronic acid (HA) hydrogel fibers in dry (e), wet (f) and re-hydrated form (g). Bars represent mean±s.d. (n=3);

FIGS. 4a-4f show small angle x-ray scattering (SAXS) patterns for fibrin and gelatin hydrogel microfibers: (a-b) SAXS patterns of dry (a) and wet (b) fibrin hydrogel fibers prepared by electrostretching; (c) SAXS pattern for fibrin hydrogel samples prepared by simple extrusion; (d-e) SAXS patterns of dry (d) and wet (e) gelatin hydrogel fibers prepared by electrostretching; and (f) SAXS pattern for gelatin hydrogel samples prepared by simple extrusion;

FIG. 5 shows an illustration of polymer alignment as a result of electrical and mechanical stretching. An aqueous solution of biopolymer(s) with or without cells is spun under electrical and mechanical stretching forces. Polymer chain alignment induced during this process is then quickly fixed with stabilizing solution in the collection bath. Bicomponent or multicomponent hydrogel fibers can be spun similarly by mixing different polymers in the spinning solution, also referred to herein as the starting solution. Additional crosslinking can be performed via enzyme, UV-initiated crosslinking, or cell compatible chemical reactions (e.g. the Michael addition reaction). Cell encapsulation can be achieved by incorporating cells in the spinning solution, forming "cellular strings"; and FIG. 6 shows tensile moduli of wet alginate hydrogel fibers prepared at different collection plate rotation speeds. All fiber samples were crosslinked in 25 mM $CaCl_2$ solution for 4 minutes prior to measurement. Bars represent mean±s.d. (n=3).

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter provides an approach that combines an electrical and mechanical stretching force to generate biopolymer hydrogel microfibers having a high degree of chain alignment within the hydrogel fiber. The presently disclosed methods can be applied to a wide range of polymer hydrogel systems, such as alginate, fibrin, gelatin, collagen, hyaluronic acid, chitosan, and their blends and are applicable to a wide range of biomedical applications.

The presently disclosed subject matter demonstrates that this internal polymer chain alignment affords excellent mechanical properties to these hydrogel fibers. The presently disclosed methods are highly versatile with a high degree of control over fiber diameter and fiber constructs. Further, the presently disclosed fiber spinning process is conducted in aqueous solutions at room temperature and is thus amenable to cell encapsulation within the hydrogel fibers during spinning and gelation.

Further, the presently disclosed subject matter demonstrates that the alignment topography is a strong matrix cue to induce alignment of cells that are seeded either inside the hydrogels or on the hydrogel surface. Due to the excellent cellular responses and the versatility of materials choice, these systems can be useful substrates to create "cellular wires" (e.g., nerve cables) or guide cell migration in wound healing or regeneration.

I. Methods of Preparing Electro-Mechanically Stretched Microfibers

Current electrospinning methods known in the art for producing microfibers rely on electrical force to stretch the fiber into a smaller diameter. In such methods, dried fiber is collected after an accelerated stretching process, during which the speed and amount of jet elongation induced by an applied electrical field is not well controlled. The high stretching rate (e.g., $10^5$ to $10^6$ $s^{-1}$) at the end of such processes also makes known electrospinning techniques unsuitable for treating delicate substances, such as hydrogel, cells, or self-assembled molecules. Further, large fibers, e.g., fibers having a diameter ranging from tens to hundreds of microns, are not easy to make by electrospinning methods known in the art.

A certain level of molecular orientation, however, can be developed via conventional electrospinning processes. Molecular level alignment in these cases is a result of high strain rate commonly used in electrospinning of polymers (e.g., $10^5$ to $10^6$ $s^{-1}$). According to theoretical models, a high degree of uniaxial orientation is expected if the product of strain rate and the conformational relaxation time λ is greater than unity during uniaxial stretching of polymeric melts or solutions. Generally, a high level crystalline structure along the fiber axis is not observed in fibers formed by conventional electrospinning processes because of the rapid solidification of the fluid jet.

In contrast, the presently disclosed methods use a combination of electrical and mechanical force to induce stretching to replace the uncontrollable stretching in electrospinning. More particularly, the presently disclosed methods use an electrical field to initiate and stretch a jet stream of polymer solution and a mechanical force exerted by a moving, e.g., rotating, collection bath comprising a stabilizing collection solution and a moving, e.g., rotating, collection plate to control the amount of stretching. In this way, the overall stretching rate can be adjusted by changing the speed of the rotating, collection plate and by modifying electric field strength. Fibers produced this way also have a molecular level preferential alignment, which significantly improves their mechanical properties.

Generally, in the presently disclosed methods, a high voltage electrode is contacted with a starting solution to initiate a jet stream of polymer solution through, for example, a syringe needle. In some embodiments, the jet stream of polymer solution is collected with a moving, e.g., rotating, collection plate positioned at a close distance to the tip of the syringe needle before the jet stream of polymer solution is accelerated by an electrical field induced by the high voltage electrode. More particularly, as provided herein above, the electric field initializes the stretching of the polymer stretch, which is due to an acceleration of the jet stream of polymer caused by the applied electrical field. The collection of the jet stream of the polymer solution occurs while the stream is still in a linear trajectory before the chaotic bending instability (whipping) regime that is standard to traditional electrospinning.

During collection, the rotating collection plate further stretches the jet stream of polymer solution so it travels the same distance as the rotating collection plate. Because the mechanical stretching rate is determined by the speed of the rotating collection plate and solution feed rate, the presently disclosed methods can be regulated to process delicate substances or to produce fibers of desired size range (10 to 300 μm), both of which cannot be done with conventional electrospinning methods known in the art.

In other embodiments, the jet stream of polymer solution is collected on a stationary collection plate and it is deposited on the stationary collection plate using a moving dispensing nozzle.

In the presently disclosed methods, the jet stream of polymer solution is collected in regions where the jet stream is initiated and before it is accelerated into a whipping jet. The overall electromechanical strain rate is estimated to be around 10 to 70 $s^{-1}$, which is several orders of magnitude lower than conventional electrospinning. The relative high molecular weight of natural polymers used in this process, corresponding to a longer relaxation time $\lambda$, will be sufficient to facilitate polymer chain alignment under low strain rate, in absence of rapid solidification.

Accordingly, the elongational flow induced by electrical and mechanical stretching force also creates a unique alignment among the individual fibers in the string or film produced. Without wishing to be bound to any one particular theory, it is thought that the synergy of electrical field and mechanical stretching helps to align the fibers. In addition to stretching induced alignment, the electrical field also contributes to the overall alignment of the fibers. The alignment can be fixed, for example by crosslinking the fibers after they are collected. Such alignment not only enhances the mechanical properties of the final matrix, but also brings new capacities for their utility. Polarized optical microscopy and scanning electron microscopy (SEM) have been used to confirm these characteristic structures.

Fibers formed by the presently disclosed subject matter can be further elongated with mechanical force along the fiber axis. Application of such mechanical force or stress helps to enhance the alignment of the polymer chains and fix them in a longitudinal direction. Due to their large surface areas, such strings will bundle together if taken out the collection or fixing solution. Applying a constant stretching force until the fibers are dry can lead to a fiber cross sectional area that decreases to approximately 2% of its original cross sectional area. Again, without wishing to be bound to any one particular theory, it is thought that such a dehydration process further improves the alignment inside the string.

Accordingly, in some embodiments, the presently disclosed subject matter provides methods to incorporate anisotropic topography inside a hydrogel matrix using a combination of electrical and mechanical stretching. Such microfibers can be made of natural polymers including, but not limited to, alginate, fibrinogen, gelatin, collagen, hyaluronic acid (HA), chitosan chondroitin sulfate, dextran sulfate, heparin, heparan sulfate, and the like, and functionalized derivatives thereof; synthetic polymers including, but not limited to, polyacrylic acid derivatives, polyvinyl alcohol, and the like.

The presently disclosed methods are versatile and scalable and represent the first approach to enable control over hydrogel alignment topography in polymer hydrogel fibers derived from a variety of biopolymers. Accordingly, the molecules inside microfibers made by the presently disclosed methods are preferentially aligned along the microfiber axis. The unique internal uniaxial alignment characteristic enhances the mechanical properties of the hydrogel microfibers. Microfibers having a size ranging from a few microns to hundreds of microns have been made using the presently disclosed electro-mechanical stretching method. The presently disclosed methods can be used to produce various forms of hydrogel matrices, such as a film, mesh, tube, a single string, or a bundled yarn.

Further, in the current state of the art, mechanical strain usually generates dense materials through the exclusion of water during the stretching process. In contrast, the presently disclosed methods retain the hydration ratio or water content throughout the spinning process. As a result, hydrogel fibers with a water content of more than 90%, and, in some embodiments, as high as 99%, including 90%, 91%, 92%, 93%, 94%, 95%, 96%, 97%, 98%, and 99% water content, can be made.

In other embodiments, twisted yarn can be produced from the hydrogel strings described hereinabove. To make a yarn, a multiround of the loop is taken out of the fixing solution and hung in the air with a weight applied at the bottom of the string. The string will elongate under such weight. The string can be elongated much more when the stretching is done at low dehydration degree. This process helps to further align the fibers. If this is done after significant crosslinking, then the deformation is limited. For example, a dried yarn of alginate is very strong and has a Young's modulus of up to 10 GPa. Such dried strings can be rehydrated after being placed back into water.

Accordingly, in some embodiments, the presently disclosed subject matter provides a method for preparing a microfiber having a uniaxial alignment, the method comprising: (a) providing at least one starting solution comprising one or more polymers; (b) applying an electrical potential to the at least one starting solution sufficient to initiate a jet stream of polymer solution; and (c) mechanically stretching the jet stream of polymer solution during or after collecting the jet stream of polymer solution in a collection bath comprising a stabilizing solution, wherein the collection bath is positioned at a separation distance such that the jet stream of polymer solution is collected before it is accelerated by an electrical field created by the applied electrical potential.

In other embodiments, the collection bath comprises a moving, e.g., rotating, collection plate, wherein a movement, e.g., a rotation, of the collection plate mechanically stretches the jet stream of polymer solution as it is collected thereon. In still other embodiments, the collection bath comprises a stationary collection plate, wherein the jet stream of polymer solution is deposited on the stationary collection plate using a moving dispensing nozzle to mechanically stretch the jet stream of polymer solution as it is deposited on the stationary collection plate. In some embodiments, one or more polymers comprise a natural polymer. In other embodiments, the natural polymer is selected from the group consisting of water-soluble polysaccharides, proteins, and combinations or blends thereof. In particular embodiments, the natural polymer is selected from the group consisting of one or more of alginate, fibrinogen, gelatin, collagen, hyaluronic acid (HA), chitosan, chondroitin sulfate, dextran sulfate, heparin, heparan sulfate, functionalized derivatives thereof, and combinations or blends thereof.

In yet other embodiments, one or more polymers comprise a synthetic polymer. In some embodiments, the synthetic polymer is selected from the group consisting of a polyester and a polyamide. In other embodiments, the polyester is selected from the group consisting of polylactic acid and poly(lactic-co-glycolic) acid. In particular embodiments, the synthetic polymer is selected from the group consisting of a polyacrylate, a poly(vinyl alcohol), a poly (ethylene glycol), functionalized derivatives thereof, and combinations or blends thereof.

In some embodiments, the starting solution further comprises a thickening agent capable of increasing a viscosity of the jet stream of polymer solution. In particular embodiments, the thickening agent comprises polyethylene glycol (PEG).

In other embodiments, the method further comprises crosslinking the microfiber. In particular embodiments, the crosslinking is selected from the group consisting of ionic crosslinking, ultraviolet crosslinking, enzymatic crosslinking, and a chemical crosslinking reaction. In some other embodiments, the method further comprises adding a crosslinking agent to the starting solution comprising one or more polymers. In still other embodiments, the method further comprises adding a crosslinking agent to the jet stream of polymer solution after the jet stream of polymer solution is initiated by the applied electrical potential. In further embodiments, the method comprises adding a crosslinking agent to the collection bath.

In particular embodiments, the electrical potential has a range from about 2 kV to about 6 kV.

In some embodiments, the stabilizing solution comprises a solvent in which the jet stream of polymer solution is insoluble and precipitates in the stabilizing solution. In other embodiments, the jet stream of polymer solution comprises an aqueous solution and one or more water-soluble polymers and the stabilizing solution comprises an organic solvent.

In yet other embodiments, the method further comprises elongating the microfiber by applying mechanical stress along the uniaxial alignment thereof, and drying the microfiber.

In some embodiments, the method further comprises combining multiple microfibers to form a fiber bundle.

In other embodiments, the at least one starting solution comprises a blend of two different polymers; or two starting solutions are provided, wherein each starting solution comprises a different polymer; and the microfiber comprises a bicomponent fiber having a core and a sheath.

In some embodiments, the method further comprises adding one or more bioactive agents to at least one starting solution. In other embodiments, the method further comprises depositing one or more bioactive agents on the microfiber after it is formed.

In still other embodiments, the method further comprises adding one or more cells to at least one starting solution. In further embodiments, the method further comprises seeding the microfiber with one or more cells on a surface of the microfiber after it is formed.

In yet other embodiments, the presently disclosed subject matter provides a microfiber formed by the presently disclosed methods. In some embodiments, the microfiber has a diameter ranging from about 5 microns to about 300 microns.

In some embodiments, the microfiber comprises more than one polymer. In other embodiments, the microfiber comprises a bicomponent fiber comprising a core and a sheath.

In further embodiments, the microfiber comprises a hydrogel. In still further embodiments, the hydrogel has a water-content of greater than about 90%. In other embodiments, the hydrogel has a water-content of greater than about 95%. In still other embodiments, the hydrogel has a water-content of greater than about 98%.

In some embodiments, the microfiber has internal molecular chain alignment.

In other embodiments, the microfiber further comprises one or more bioactive agents. In still other embodiments, the microfiber further comprises one or more cells.

In other embodiments, bioactive agents may be either post-loaded in the microfibers or loaded in situ within the microfiber as a component of the starting polymer solution, wherein the bioactive agents may include, but are not limited to, therapeutic agents, nanoparticles, water soluble proteins, cells, and their like. In still other embodiments, the bioactive agents are used for localized, sustained release in vitro or in vivo.

II. Use of Electro-Mechanically Stretched Microfibers as Scaffold Materials for Cell or Tissue Growth A highly endeavored topic in regenerative medicine is to create extracellular matrix (ECM) analogs for providing mechanical supports and biochemical cues to cells. For cases such as tendons, nerves and corneal stroma and intervertebral-disc regeneration, a matrix that can guide cellular alignment and growth direction is essential for optimal results.

Many new scaffold materials have been developed for such purposes. For example, Zhang et al. have developed self-assembly peptide hydrogel strings that can align encapsulated cells and others also have used electrospun nanofibers to guide cellular growth direction. Aligned ECM made from natural polymer fibers, which in many cases possess unprecedented biological performance, are limited, however, to microfluidic alignment, cyclic mechanical stretching, and the like.

The facile, organic solvent-free processing conditions of the presently disclosed methods are amenable to the incorporation of live cells and/or growth factor proteins within the hydrogel fiber or on the fiber surface and effectively induce cellular alignment and provide cellular growth guidance.

Accordingly, in some embodiments, the presently disclosed microfiber having a uniaxial alignment can be used as a template for growing and guiding cells. The presently disclosed microfibers also can incorporate encapsulated cells and/or growth factor proteins. Such microfibers can be used for making a cellular guide, a nerve guide for neuronal regeneration, a template for growing micro-blood vessels, surgical sutures, wound dressing, or tissue scaffolds for tissue engineering.

In further embodiments, a co-axial spin of a hydrogel core/sheath structure with cellular content in the core also can be produced.

In a representative example, the electro-mechanically stretched hydrogel string can be used to direct the orientation of cells trapped inside. After dispersing mammalian cells in alginate/fibrinogen mixture solution, the hydrogel strings can be stretched and collected in 50 mM $CaCl_2$ and 5-20 units/mL thrombin solution to form hydrogel fibers with encapsulated cells. The facile spinning condition will ensure that the encapsulated cells remain viable during the process of fiber formation and culture.

In other embodiments, the same cells can be cultured on the surface, as well. It is obvious to those skilled in the art that these cells can align with the axis of the fiber.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Preparation and Characterization of Hydrogel Microfibers

To produce alginate hydrogel microfibers, 2-6 kV, 1.5-3.0 wt % alginate and 0.1-0.6 wt % PEG solution were used. The alginate hydrogel microfibers were stabilized in a collection bath comprising 20 mM to 100 mM $CaCl_2$ and a rotating collection plate. As a representative example, a starting solution comprising 2.0 wt % alginate (from brown algae, approximately 250 cps viscosity for a 2% solution at 25° C.) and 0.2 wt % poly(ethylene glycol) (PEG, average My ca. 4,000 kDa, Sigma Aldrich, St Louis, Mo.) is used. The starting solution was pumped through a 27 gauge needle syringe at 2 mL/hour rate by a syringe pump. A 3-kV voltage was applied to the needle with a clamp from a high voltage power source (Gamma High Voltage Research, Ormond Beach, Fla.). The rotating collection plate in the collection bath has a diameter of about 20 cm and rotates at about 25 rpm. The rotating collection plate was positioned approximately 4 cm away from the exit of the syringe needle. The 50 mM $CaCl_2$ solution stabilizes the alginate hydrogel fibers during collection. After the hydrogel strings are collected on the rotating collection plate, they are allowed to crosslink in the 50 mM $CaCl_2$ solution for 3 min before use.

With similar flow rates and applied voltages, fibrin, gelatin and HA hydrogel fiber bundles also were prepared. In representative examples, fibrin hydrogel fibers were produced using an aqueous solution that contains 0.7 wt % fibrinogen, 1.0 wt % sodium alginate and 0.1 wt % PEG. Upon collection, the hydrogel fibers were crosslinked in 50 mM $CaCl_2$ with 5 Units/mL thrombin for 20 minutes. If necessary, a higher concentration of thrombin can be used to shorten the crosslinking time.

As another representative example, aqueous solutions that contain 2.0 wt % fibrinogen from bovine plasma (syringe 1) and 1.5 wt % sodium alginate/0.2 wt % PEG (syringe 2) were mixed through a Y junction mixer at 1:2 ratio. The mixed solution was pumped through a 25 gauge needle syringe at 3 mL/hour rate. A 4 kV voltage was used to initiate the electrostretching process. Upon collection, hydrogel fibers were crosslinked in $CaCl_2$/thrombin solution (50 mM, 5 Units/mL) for 20 minutes. After crosslinking, the hydrogel microfibers were soaked in 250 mM sodium citrate solution overnight to remove alginate and PEG. The hydrogel microfibers were then rinsed with distilled water to remove the sodium citrate residue before use.

As an alternative to the protocol disclosed immediately hereinabove, fibrinogen and PEG (1 wt %/0.1 wt %) were directly mixed and processed at 4 kV voltage. The crosslinking solution in this case contained 50 mM $CaCl_2$ and 20-unit/mL thrombin. After 20 minutes of crosslinking, the hydrogel microfibers can be directly collected for use.

Gelatin hydrogel fibers were prepared with 3.2 wt % methacrylated gelatin, 0.9 wt % sodium alginate, 0.1 wt % PEG, and 0.4 wt % photo initiator Irgacure 2959, followed by crosslinking with 50 mM $CaCl_2$ solution for 5 minutes and then UV-irradiation at $\lambda$ 365 nm for 10 minutes. Methacrylated gelatin was prepared according to a previously reported protocol (Nichol et al., 2010). As another representative example, gelatin hydrogel fibers were prepared with a solution containing 3.0 wt % methacrylated gelatin, 1.0 wt % sodium alginate, 0.15 wt % PEG and 0.4 wt % photo initiator Irgacure 2959 (CIBA Specialty Chemicals, Basel, CH). Flow rate was set as 2 mL/hour. Other processing parameters were similar to the generation of alginate and fibrin described hereinabove. Upon collection, alginate was crosslinked in 50 mM $CaCl_2$ bath for 5 minutes. UV-irradiation at $\lambda$ 365 nm with Mineralight Lamp UVGL-25 (UVP LLC, Upland, Calif.) was then used to crosslink the gelatin for 10 minutes. After crosslinking, 250 mM sodium citrate solution was used to remove alginate, PEG and photo initiator overnight. Distilled water was then used to rinse off the sodium citrate residue before use.

Similarly, HA hydrogel fibers were prepared with 1 wt % thiolated HA, 0.7 wt % alginate and 0.2 wt % PEG, and crosslinked with 50 mM $CaCl_2$ and 1 wt % polyethylene glycol diacrylate (PEGDA). As another representative example, HA hydrogel fibers were prepared with 1.0 wt % thiolated HA (Glycosan BioSystems Inc.), 0.75 wt % alginate and 0.2 wt % PEG solution. A 4-kV applied voltage was used to initiate the jet. The flow rate used was 2 mL/hour. The collection bath contained 50 mM $CaCl_2$ and 1 wt % PEGDA to crosslink alginate and HA. After 20 minutes of crosslinking, alginate, PEG and excess PEGDA can be removed by sodium citrate and distilled water, using the protocols for generating alginate and fibrin described hereinabove.

Collagen hydrogel fibers were prepared with 2.0 wt % methacrylated collagen (Syringe 1) and 1.5 wt % sodium alginate/0.2 wt % PEG/0.4 wt % photo initiator Irgacure 2959 (Syringe 2). These solutions were mixed through a Y junction mixer at a 1:1 ratio. The combined solution was pumped through a 25-gauge needle syringe at 3 mL/hour rate. 4 kV applied voltage was used to initiate the jet. The collection bath contained 50 mM $CaCl_2$. Upon collection, the alginate was crosslinked in the 50 mM $CaCl_2$ bath for 5 minutes. UV-irradiation at $\lambda$ 365 nm was then used to crosslink collagen for 10 minutes. After crosslinking, 250 mM sodium citrate solution was used to remove alginate, PEG and photo initiator overnight. Distilled water was then used to rinse off the sodium citrate residue before use.

Methacrylated collagen used in this example was prepared by adding methacrylic anhydride to acid solubilized type I collagen (3 mg/mL, Life Technologies, Carlsbad, Calif.). Before reaction, the collagen solution was adjusted to pH 7.5 with 0.2 M $Na_2HPO_4$ buffer. Methacrylic anhydride (MA) was added in different ratios to obtain a desired degree crosslinking capacity. After an eight-hour reaction, the mixture was dialyzed against 10 mM HCl for 2 days. Pierce Slide-A-Lyzer Concentrating Solution (Thermo Scientific, Waltham, Mass.) was used to condense the solution to the desired concentration.

Dehydrated String Bundles.

Dehydrated string bundles known in the art typically are produced by air-drying. Applying an axial stress can exclude the liquid content, speed up the drying process, and enhance alignment. As a representative example, fibrin hydrogel strings collected by the protocol disclosed hereinabove was stretched to 160% of its original length and air-dried. Alginate hydrogel string collected as described hereinabove also was stretched to 130% of its original length and air-dried. In both cases, the hydrogel strings shrank in diameter and became dehydrated thin strings. Their average Young's modulus also drastically increased to 10 GPa for calcium alginate fibers and 2 GPa for fibrin fibers. Hydrogel strings of other compositions can be dehydrated in a similar way. Alternatively, hydrogel strings can be frozen and lyophilized to create a porous morphology. Dehydrated strings made by both methods can be rehydrated when soaked in water.

SEM Analysis.

Hydrogel microfiber samples were first serially dehydrated in 50%, 60%, 70%, 80%, 90%, 95% and 100% ethanol for 15 minutes in each solution, critical point dried, and then sputter-coated with 8-nm thick Au/Pd. Samples were imaged on a JEOL 6700F field-emission SEM (Tokyo, Japan).

Small and Wide Angle X-Ray Scattering.

SAXS experiment was performed at the Cornell High Energy Synchrotron Source (CHESS; Ithaca, N.Y., USA). Dry or wet hydrogel fibers were subjected to 10-second exposures of the synchrotron beam ($\lambda$=0.11521 nm, beam size: 0.5 mm horizontal×0.1 mm vertical) for 10 times. A 48 mm×48 mm 2-D CCD detector with pixel size of 46.9 μm×46.9 μm was used to collect the scattering data. The averaged intensity readings on each pixel of the detector were recorded and analyzed with fit2D. WAXS experiments were performed using a Rigaku R-Axis Spider Diffractometer (Rigaku Americas Corp., The Woodlands, Tex., USA) with an image plate detector and a graphite monochromator using Cu K$\alpha$ radiation ($\lambda$=0.15418 nm). The instrument was controlled by Rapid/XRD diffractometer control software (version 2.3.8, Rigaku Americas Corp., The Woodlands, Tex., USA). Fibers were grouped into a bundle and secured on the sample stage. Two-dimensional diffraction data were collected for 20 minutes while rotating the sample stage at 5° per minute. The 2D diffraction data were radially integrated with 2DP Spider software (version 1.0, Rigaku Americas Corp., The Woodlands, Tex., USA).

Mechanical Testing.

Single axial stretching tests were performed over the hydrogel microfibers in dry, wet and rehydrated forms with a DMA Q800 unit from TA Instruments (New Castle, Del., USA). Experiments results revealed that, while dry fibers have limited capacity to elongate (approximately 3-5% strain at break), wet hydrogel fibers were stretched to more than 100% strain before breaking. The average Young's moduli of dry calcium alginate, fibrin, gelatin and HA fibers were 10.0 GPa, 2.2 GPa, 0.8 GPa, and 3.0 MPa, respectively. For wet fibers prior to the drying step, the Young's moduli were several orders of magnitude lower (717 kPa, 37.3 kPa, 2.6 kPa, and 1.3 kPa, respectively). The moduli of rehydrated fibers fell in between the two sets, with 108 MPa, 289 kPa, 4.4 kPa, and 58.5 kPa, respectively. In these analyses, sample diameters were determined using a light microscope. For wet strings, samples were stretched to break within 30 seconds to minimize the effect of water evaporation on measurement. The Young's moduli were calculated within the initial linear region of the stress-strain curves from the tests.

Example 2

Electromechanical Stretching Setup and Features

This strategy employs electrical and mechanical stretching to induce polymer chain alignment during spinning of an aqueous polymer solution, followed by rapid chain alignment fixation of the polymer jet via crosslinking (FIG. 1a). The electrostretching setup includes a collection bath comprising a crosslinking solution and a grounded, motor-driven rotating collection plate. The polymer jet is charged with a relatively lower electrical potential of 2-6 kV, including 2, 3, 4, 5, and 6 kV and any fractional value within the range of 2-6 kV, than typically applied for electrospinning methods known in the art (5-30 kV).

In some embodiments, the presently disclosed electromechanical stretching platform includes a high voltage power supply, a needle syringe pump, a syringe, and a motor-run rotating metal disc, i.e., the collection plate. The collection plate can have a diameter of about 20 cm. A high voltage DC power is applied to the solution by clamping an electrode on the syringe needle. The applied voltage is about 2-6 kV, and the flow rate of the solution is about 0.4-4 mL/hour. After the jet is initiated by applying the electrical potential, the stretched string is collected on the collection plate, which can be positioned about 3 cm to 5 cm away from the exit of the syringe needle in a calcium chloride solution reservoir, i.e., the collection bath. The angular velocity of the collection plate is controlled by a DC motor controller (Dart 15DVE) unit, which was usually operated in a range from about 20 to 80 rotations/minute. If more than one solution is involved, such as co-spinning of multiple components or co-axial spinning, an additional syringe pump can be used.

In some embodiments, the hydrogel fiber is made from alginate. The good biological compatibility and high viscosity of alginate makes it not only a good candidate to make hydrogel string by itself, but also makes it an ideal template to induce stretching over other materials.

The entire process is conducted in aqueous solutions. For example, a solution of sodium alginate (1.5-3.0 wt %) and polyethylene glycol (PEG, 0.1-0.6 wt %) is charged with 2-6 kV positive potential and extruded through a syringe needle at a flow rate of 1-3 mL/h. The PEG in the alginate solution serves as a thickening agent to increase the viscosity of the alginate solution jet (Ji et al., 2006). The electrical field causes the polymer solution to form a jet. The jet is further stretched upon being collected on the rotating collection plate containing 20-100 mM $CaCl_2$ solution at a collecting distance approximately 3-6 cm from the needle tip. The diameter of the collected hydrogel fiber can be tuned by adjusting the solution extrusion rate and the angular velocity (20-80 rpm) of the rotating collection plate, which in embodiments where the diameter of the rotating collection plate is 20 cm, corresponds to a linear velocity of about 20-84 cm/second. The fiber diameter increases with solution extrusion rate and decreases with rotation velocity of the rotating collection plate. For example, the average diameter of individual calcium alginate fibers can be controlled in the range of 17 μm to 116 μm by varying the flow rate of alginate (2 wt %)—PEG (0.2 wt %) solution from 0.7-7 mL/hour at room temperature (FIG. 1b). Hydrogel fibers produced with this process have highly uniform diameters (FIG. 1c), and continuous hydrogel microfibers of any length can be produced. Further, the hydrogel microfibers can be grouped together to form bundles of tunable diameters depending on the number of individual fibers used.

The versatility of the presently disclosed approach can be demonstrated by preparing internally aligned hydrogel microfibers from several natural polymers (alginate, fibrin, gelatin (Nichol et al., 2010) and hyaluronic acid (Shu et al., 2004)) using different crosslinking schemes (FIG. 1c-f). Calcium alginate hydrogel fibers were initially prepared. One important advantage of the calcium alginate hydrogel system is its fast gelation rate. Potter et al. have determined the displacement of the crosslinking reaction front in 2 wt % alginate solution to be approximately 20 μm/second in a 50 mM $CaCl_2$ crosslinking solution, and 40 μm/second in 100 mM $CaCl_2$ (Potter et al., 1994). In the electrostretching system described above, a 40-μm alginate fiber can be effectively crosslinked in about 0.5-1.0 seconds by the $CaCl_2$ solution. This fast crosslinking scheme allows the incorporation of other water-soluble polymers to form polymer blend fibers. Additional enzyme-, UV- or chemical-mediated crosslinking reactions can be used together with calcium ions to further stabilize the hydrogel fibers. In some embodiments, thrombin-mediated crosslinking of fibrinogen can be used to form fibrin-alginate blend fibers, UV light can be used to crosslink methacrylated gelatin-alginate fibers, and a Michael-type addition reaction can be used to crosslink thiolated hyaluronic acid-alginate fibers (FIG. 1d-f). After crosslinking, alginate and PEG can be removed from the polymer blend hydrogel fibers by washing the fibers with sodium citrate. All of these crosslinking and washing steps can be carried out in aqueous buffers under ambient conditions and therefore are cell-compatible.

Additional components, such as cells and bioactive agents, can be included by mixing them with the polymer solution or through an additional syringe pump. End point mixing nozzle or co-axial stretching nozzle also can be used. In some embodiments, fibrinogen is mixed with alginate and the mixture is co-crosslinked with $CaCl_2$ and thrombin. In other embodiments, gelatin and hyaluronic acid strings are formed by mixing methacrylated gelatin or acrylated hyaluronic acid with alginate and co-crosslinking with $CaCl_2$, photo initiator Irgacure 2959 and UV light. In these embodiments, alginate is used as a template material and can be dissolved in calcium sequester solution, such as sodium citrate, EDTA or even PBS solution for fast or slow alginate removal.

Electrostretched hydrogel microfiber bundles are mechanically stronger and easier to handle than the typical hydrogels of the same composition and size. As a demonstration, an electrostretched calcium alginate hydrogel fiber bundle was used to lift a 10-g metal weight (FIG. 1i), and also two individual alginate gel strings were tied into a micro-knot using forceps (FIG. 1j). On the contrary, bulk alginate hydrogels or alginate fibers prepared with the same concentration of alginate, but without employing the presently disclosed stretching process cannot withstand such manipulations. Due to the improved mechanical property and ease of handling, such hydrogel materials can be further fabricated into other forms like films, tubes and more (FIGS. 1l-m).

To probe the structural origin for enhanced mechanical properties, birefringence imaging of the electrostretched hydrogel fibers was conducted. The extinction of light at the cross-point of fibers (FIG. 1k) indicated strong polymer chain alignment within the hydrogel microfiber bundles.

Example 3

Figure 2:
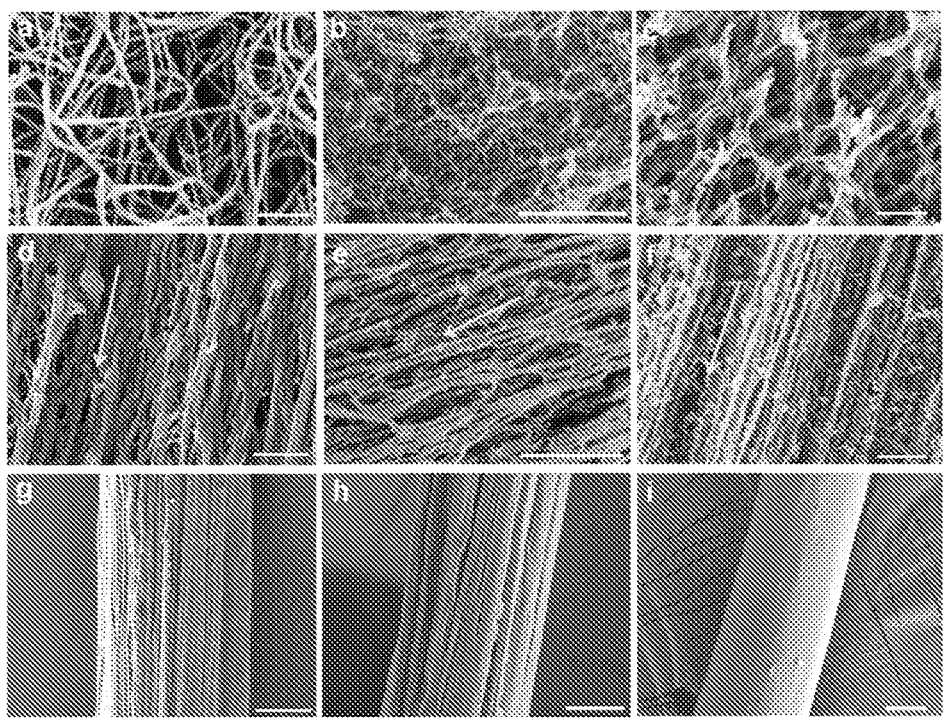

Scanning Electron Microscope Images and Small Angle X-Ray Scattering (SAXS) Patterns The alignment structure was further confirmed on critical point-dried hydrogel microfiber bundles utilizing scanning electron microscope (SEM; FIGS. 2a-2i). As shown in FIG. 2a-c, fibrin, methacrylated gelatin, and thiolated HA hydrogels prepared using simple mixing and crosslinking steps formed random nanofiber mesh networks. In contrast, the electrostretched hydrogel microfibers exhibited preferential alignment along the fiber axis (FIG. 2d-f). Such highly porous and aligned surface texture also is very different from recently developed fibrin microthreads, which are dense and smooth on the surface (Cornwell and Pins, 2007; Grasman et al., 2012). Grouping of individual fibers into bundles followed by further stretching (usually 30-100% of the initial length) and dehydration resulted in dense microfibers with aligned grooves and surface textures (FIG. 2g-h). These dry fibers can be rehydrated to about 50-100% of their original diameter depending on their drying processes.

Figure 3:
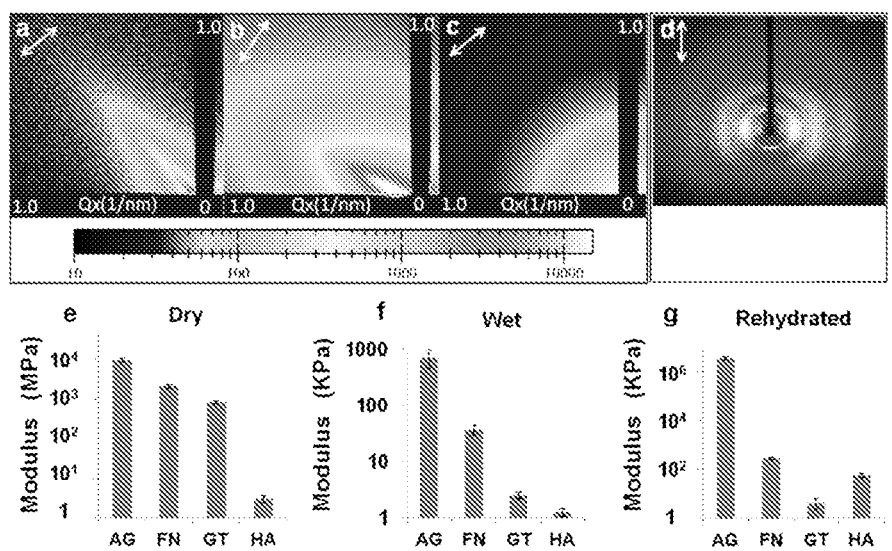
Figure 4:
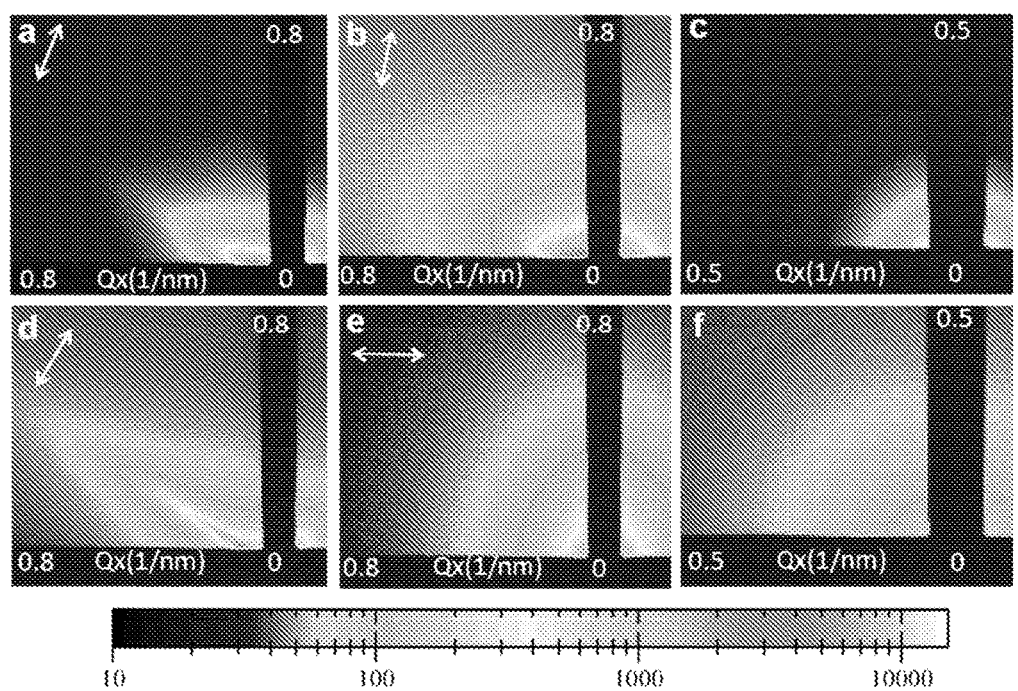

To confirm molecular alignment within the hydrogel fibers, both in dry and hydrated forms, their small angle X-ray scattering (SAXS) patterns were analyzed (FIG. 3a-b), which showed strong anisotropic scattering profiles, indicating preferential orientation along the fiber axis. As a comparison, both dry and hydrated non-stretched alginate samples gave an isotropic scattering pattern (FIG. 3c). The wide-angle X-ray scattering (WAXS) analysis of dry calcium alginate microfibers also showed a reflection profile that was indicative of an oriented polymer crystalline phase (FIG. 3d). The reflection pattern also confirmed that the polymer chains are oriented preferentially along the microfiber axis indicated by the arrow. Results with fibrin and gelatin strings are similar to that of calcium alginate (FIG. 4).

The preferential alignment of polymer chains within the microfibers greatly improved mechanical properties of the hydrogel fibers. FIG. 3e-g shows the Young's moduli of dry, wet, and hydrated hydrogel fiber bundles. While dry fibers have limited capacity to elongate (approximately 3-5% strain at break), wet hydrogel fibers were stretched to more than 100% strain before breaking. The average Young's moduli of dry calcium alginate, fibrin, gelatin and HA fibers were 10.0 GPa, 2.2 GPa, 0.8 GPa, and 3.0 MPa, respectively. For wet fibers prior to the drying step, the Young's moduli were several orders of magnitude lower (717 kPa, 37.3 kPa, 2.6 kPa, and 1.3 kPa, respectively). On the other hand, the moduli of rehydrated fibers fell in between the two sets, with 108 MPa, 289 kPa, 4.4 kPa, and 58.5 kPa, respectively. According to the theory proposed by MacKintosh et al., the modulus of an entangled network scales with concentration (MacKintosh et al., 1995). Therefore, the modulus and stiffness of the hydrogel fibers can be further adjusted by varying the concentration of starting materials, such as alginate and fibrinogen, and crosslinking density. As substrate modulus plays an important role in regulating cellular behaviors like proliferation, migration and differentiation, the ability to tune hydrogel fiber modulus and stiffness over such a wide range makes the presently disclosed hydrogel fiber matrix versatile for a wide range of applications (Engler et al., 2006; Discher et al., 2005). These analyses confirm that hydrogel fibers prepared by electrostretching exhibit polymer chain alignment along the microfiber axis. In contrast, hydrogel samples prepared by simple extrusion have an isotropic structure.

The relatively low electrical potential applied to the polymer solution (a measured current of 4-6 µA), the aqueous solvent, and ambient crosslinking conditions make this process compatible with cell encapsulation. In some embodiments, alginate is not a favorable cell scaffold matrix due to the lack of cell adhesion moieties. Therefore, in some embodiments, fibrin, gelatin or hyaluronic acid are blended into the hydrogel fibers, each employing a unique second crosslinking step to further stabilize the hydrogel fiber matrix. For example, a solution of fibrinogen, alginate, and PEG can be mixed with cells, and subjected to the electrostretching condition as described above.

Hydrogel fibers are rapidly crosslinked by the calcium solution in the collection bath, followed by crosslinking of fibrinogen into fibrin network with thrombin. Similarly, methylated gelatin and thiolated HA can be used instead of fibrinogen using the corresponding crosslinking methods discussed in FIG. 1 (detailed conditions are listed in Table 1; all fibers described in Table 1 were spun at 3-5 kV electrical potential and collected on a rotating collection plate spun at 20-80 rpm). All these crosslinking methods are cell-compatible. After the second crosslinking step, alginate and PEG can be removed with sodium citrate, if a higher degree of porosity is desired.

TABLE 1

Spinning Parameters for different Hydrogel Microfibers

| Hydrogel Composition | Spinning Solution Concentration (wt %) | Crosslink Method | Crosslink Condition |
|---|---|---|---|
| Alginate | 0.75-3.0% Alginate 0.1-0.4% PEG | Ionic crosslinking | 25-100 mM CaCl$_2$ |
| Fibrin + Alginate | 0.67-2.0% Fibrin 0.25-2.5% Alginate 0.1-0.2% PEG | Enzymatic and ionic crosslinking | 5 U/mL thrombin 50 mM CaCl$_2$ |
| Gelatin + Alginate | 1.0-3.2% Gelatin 0.24-0.86% Alginate 0.40-1.0% Irgacure | Ionic & UV-crosslinking | 50 mM CaCl$_2$ 0.50% Irgacure 10 min UV at 365 nm |
| Hyaluronic Acid + Alginate | 1.0-2.0% HA 1.5% Alginate 0.1-0.4% PEG | Ionic & Michael addition crosslinking | 1% PEGDA & 50 mM CaCl$_2$ |
| Fibrin | 0.67-2.0% Fibrin 0.1-0.2% PEG | Enzymatic crosslinking | 20 U/mL thrombin |
| Collagen + Alginate | 0.67-2.0% Collagen 0.25-2.5% Alginate 0.1-0.2% PEG | Ionic & UV-crosslinking | 50 mM CaCl2 0.50% Irgacure 10 min UV at 365 nm |

Example 4

Loading Drugs or Other Bioactive Agents in Hydrogel Microfibers

The hydrogel microfibers can be loaded with drugs or other active agents in situ or through post-loading. In situ loading can be achieved by including these active agents in the polymer solution. As an example, nanoparticles or growth factors can be directly added into alginate solution at various concentrations and processed using the typical process for making the hydrogel microfibers in Example 1. The crosslinked calcium alginate network thus encapsulates the nanoparticles and growth factors inside the microfiber.

Alternatively, microfibers can be loaded with drugs or other bioactive agents by soaking either the hydrated or dehydrated microfiber in a solution containing the drugs or active agents. In one example of post-loading, alginate/fibrin blend microfibers are soaked in a solution containing growth factors at various concentrations for 12 hours, and then dried in the air.

Drugs and bioactive agents include, but are not limited to, grow factors, small molecular weight compounds that can promote cell growth, enhance cell differentiation and maturation, or facilitate cell migration and tissue organization. In some specific examples, bioactive agents are selected from glial cell-derived neurotrophic factor, nerve growth factor, bone morphogenic factor, hepatic growth factor, vascular endothelial growth factor, and the like.

Example 5

Culture Mammalian Cells with Hydrogel Microfibers

Cell Encapsulation into Hydrogel Microfibers.

Mammalian cells, including but not limited to adipose tissue-derived stem cells, Schwann cells, oligodendrocytes, etc. can be encapsulated into fibrin or fibrin-alginate hydrogel microfibers at a density of 2,000-10,000 cells/μL. To produce such cell-laden hydrogel microfibers, cells can be suspended in fibrinogen solution, which is then mixed at 1:2 volume ratio through a syringe with a solution of 1.5 wt % sodium alginate and 0.2 wt % PEG solution, and charged at +4 kV potential, and electrostretched according to the procedure described in Example 2. The collection bath can contain a stabilization solution of 50 mM $CaCl_2$, 5 Units/mL thrombin and 5% glucose to maintain the physiological osmolarity. The crosslinking step can be conducted similarly as that described in Example 2. After crosslinking, cell-laden fibers can be collected, transferred into a Petri dish with media, and cultured in 5% $CO_2$ incubator at 37° C.

Culture Cells on the Surface of Hydrogel Fibers.

Microfibers prepared by the method described here can be used as a micro-scaffold for cell culture, Mammalian cells can be seeded onto the surface of hydrogel microfibers and cultured using standard cell culture techniques.

Example 6

Discussion

The presently disclosed subject matter demonstrates that a high degree of axial alignment of polymer chains inside hydrogel microfibers can be induced by a combination of electrical and mechanical stretching effects. Polymer chain alignment induction during the electrospinning process has been previously reported (Catalani et al., 2007; Bellan and Craighead, 2008; Fennessey and Farris, 2004). For example, PEG polymer chain can be aligned when the PEG solution is subjected to a 14-kV electric potential (Kakade et al., 2007). This observed alignment arises because the PEG chain has flexible C—O ether bonds in the backbone, facilitating the PEG chain alignment along water molecule dipole orientation in response to the strong electrical field (Kakade et al., 2007). This method may not be applicable to other polymer-solvent systems, however, particularly for the presently disclosed biopolymers, which exhibit longer relaxation times and coiled chain conformations.

In the presently disclosed methods, these barriers are circumvented by reducing the electric potential and extending the jet stretching time. In some embodiments, the average air travel time of the alginate solution jet ranged from about 100 msec to about 500 msec before it was collected on a rotating collection plate in a collection bath containing the crosslinking solution, in contrast to a typical air travel time about 10 msec for the liquid jet in electrospinning before the solvent evaporation step (Reneker, 2000). Again, without wishing to be bound to any one particular theory, it is thought that this extended jet stretching time likely allows alginate chains to align better with the electric field.

In further embodiments, this electric field-induced polymer chain alignment can be further enhanced by mechanical stretching (FIG. 5). According to theoretical models, a high degree of polymer chain alignment can be achieved during the uniaxial stretching of a polymer solution jet if the Weissenberg number, defined as the product of strain rate $\dot{\varepsilon}$ and the conformational relaxation time $\lambda$, is greater than 1 (Larson and Mead, 1993). Despite the high strain rates ($10^5$-$10^6$ s$^{-1}$) commonly observed in polymer solution jets during electrospinning, high degrees of alignment are usually difficult to achieve. This difficulty is likely due to the rapid solidification of electrospun fibers under typical spinning conditions, which does not give sufficient time for polymer chains to align (Inai et al., 2005; Zong et al., 2002). In some embodiments, under the presently disclosed electrostretching conditions, the alginate solution is collected without significant solvent evaporation, and the solution jet has an estimated strain rate $\dot{\varepsilon}$ of 10-70 s$^{-1}$. Although the strain rate is not very high, it is compensated by the long relaxation time due to the high molecular weight of alginate and PEG. Thus, the mechanical shear induced by the rotating collection plate can significantly contribute to the higher degree of alignment of the polymer chain. This analysis is supported by the observation that a faster rotating velocity leads to fibers with higher tensile modulus, indicating a higher degree of alignment enhanced by stronger mechanical stretching (FIG. 6).

The Young's modulus of wet fibers increased with the angular velocity of the rotating collection plate. These results suggest that a higher degree of mechanical stretching—under a higher angular velocity of the rotating collection plate—induces a higher degree of polymer chain alignment, manifested by a higher Young's modulus.

Without wishing to be bound to any one particular theory, it is thought that the efficacy of the presently disclosed method also relies on an effective crosslinking or fixation of the induced polymer chain alignment. The presently disclosed subject matter provides different crosslinking strategies that are applicable for a wide selection of biopolymers. These crosslinking methods also are complementary so that it is possible to prepare blended fibers having different compositions to afford multi-functionalities—a feature particularly suitable for regulating cell adhesion, tissue compatibility, permeability, and surface conjugation of ligands.

Further, the biodegradability of the presently disclosed fibers can be tailored by blending polymers with different degrees of sensitivity to hydrolysis and degradative enzymes. In some embodiments, the degradation can be triggered on demand. In some other embodiments, alginate fibers can be dissolved by treating the fibers with sodium citrate solution or alginate lyase. In further embodiments, fibrin fibers can be degraded by plasmin and HA fibers can be degraded by hyaluronidase.

In some embodiments, the entire fiber spinning and crosslinking process is conducted in aqueous solutions under ambient conditions, making it amenable to cell encapsulation inside hydrogel fibers. In particular, the low electric potential (2-6 kV) in contrast to electrospinning and low mechanical shear ensure high cell viability in hydrogel fibers.

In some embodiments, the hydrogel fibers generated by the presently disclosed electrostretching method exhibit excellent mechanical properties while maintaining sufficient porosity and water content (>90%, usually 98%-99%). This characteristic is in contrast with hydrogel fibers prepared by simple extrusion, in which case polymer solutions are pressed through a small orifice and crosslinked during or after extrusion. Hydrogel fibers produced by the extrusion method do not exhibit a high degree of polymer chain alignment (FIG. 3c), and are therefore mechanically weaker and more challenging to handle than hydrogel fibers produced by electrostretching. Although this limitation in extruded fibers can be overcome by lowering the water content and increasing crosslinking density, these denser fibers are not suitable for cell encapsulation. The porosity of the electrostretched hydrogel fibers also can be easily tuned by varying the input polymer concentration, composition and crosslinking density.

Accordingly, the presently disclosed subject matter provides methods to generate hydrogel microfibers with a high degree of polymer chain alignment induced by a combination of electrical and mechanical stretching, and facilitated by the long polymer chain relaxation time, and effective crosslinking schemes. Using this concept, internally aligned hydrogel microfiber bundles of calcium alginate, fibrin, gelatin, hyaluronic acid, collagen and their blends have been produced. These microfibers exhibit enhanced mechanical properties as a result of the polymer chain alignment while maintaining high water content and porosity. The facile preparation conditions are conducive to cell encapsulation in generating "cellular strings." Due to their biodegradable nature and unique geometry and surface topography, they are ideal scaffold candidates for generating aligned tissue structures. The development of these new hydrogel fibers represents an important step toward successful fabrication of hierarchically organized cellular structures in 3D.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Aubin, H., Nichol, J. W., Hutson C. B., Bae, H., Sieminski, A., Cropek, D. M., Akhyari P., and Khademhosseini A. Directed 3D cell alignment and elongation in microengineered hydrogels. Biomaterials 31, 6941-6951 (2010);

Bellan, L. M. and Craighead, H. G. Molecular orientation in individual electrospun nanofibers measured via polarized Raman spectroscopy. Polymer 49, 3125-3129 (2008);

Bettinger, C. J., Langer, R. and Borenstein, J. T. Engineering substrate topography at the micro- and nanoscale to control cell function. Angew. Chem. Int. Ed. 48, 5406-5415 (2009);

Burdick, J. A. and Anseth, K. S. Photoencapsulation of osteoblasts in injectable RGD-modified PEG hydrogels for bone tissue engineering. Biomaterials 23, 4315-4323 (2002);

Catalani, L. H., Collins, G. and Jaffe, M. Evidence for molecular orientation and residual charge in the electrospinning of poly(butylene terephthalate) nanofibers. Macromolecules 40, 1693-1697 (2007);

Chew, S. Y., Mi, R., Hoke, A. and Leong, K. W. The effect of the alignment of electrospun fibrous scaffolds on Schwann cell maturation. Biomaterials 29, 653-661 (2008);

Coburn, J., Gibson, M., and Bandalini, P. A. Biomimetics of the extracellular matrix: an integrated three-dimensional fiber-hydrogel composite for cartilage tissue engineering. Smart Struct Syst 7, 213-222 (2011);

Cornwell, K. G. and Pins, G. D. Discrete crosslinked fibrin microthread scaffolds for tissue regeneration. Journal of Biomedical Materials Research Part A 82A, 104-112 (2007);

Dalsin, J. L., Hu, B. H., Lee, B. P. and Messersmith, P. B. Mussel adhesive protein mimetic polymers for the preparation of nonfouling surfaces. Journal of the American Chemical Society 125, 4253-4258 (2003);

Discher, D. E., Janmey, P. and Wang, Y. L. Tissue cells feel and respond to the stiffness of their substrate. Science 310, 1139-1143 (2005);

Engler, A. J., Sen, S., Sweeney, H. L. and Discher, D. E. Matrix elasticity directs stem cell lineage specification. Cell 126, 677-689 (2006);

Fennessey, S. F. and Farris, R. J. Fabrication of aligned and molecularly oriented electrospun polyacrylonitrile nanofibers and the mechanical behavior of their twisted yarns. Polymer 45, 4217-4225 (2004);

Grasman, J. M., Page, R. L., Dominko, T. and Pins, G. D. Crosslinking strategies facilitate tunable structural properties of fibrin microthreads. Acta Biomaterialia 8, 4020-4030 (2012);

Inai, R., Kotaki, M. and Ramakrishna, S. Structure and properties of electrospun PLLA single nanofibres. Nanotechnology 16, 208-213 (2005);

Ingram, D. A., Mead, L. E., Tanaka, H., Meade, V., Fenoglio, A., Morten, K., Pollok, K., Ferkowicz, M. J., Gilley, D., and Yoder, M. C. Identification of a novel hierarchy of endothelial progenitor cells using human peripheral and umbilical cord blood. Blood 104, 2752-2760 (2004);

Ji, Y., Ghosh, K., Li, B., Sokolov, J. C., Clark, R. A. F., and Rafailovich, M. H. Dual-syringe reactive electrospinning of cross-linked hyaluronic acid hydrogel nanofibers for tissue engineering applications. Macromol Biosci 6, 811-817 (2006);

Ji, Y., Ghosh, K., Shu, X. Z., Li, B., Sokolov, J. C., Prestwich, G. D., Clark, R. A. F., and Rafailovich, M. H. Electrospun three-dimensional hyaluronic acid nanofibrous scaffolds. Biomaterials 27, 3782-3792 (2006);

Kakade, M. V., Givens, S., Gardner, K., Lee, K. H., Chase, D. B., and Rabolt, J. F. Electric field induced orientation of polymer chains in macroscopically aligned electrospun polymer nanofibers. Journal of the American Chemical Society 129, 2777-2782 (2007);

Kang, E., Jeong, G. S., Choi, Y. Y., Lee, K. H., Khademhosseini, A., and Lee, S.-H. Digitally tunable physicochemical coding of material composition and topography in continuous microfibres. Nature Materials 10, 877-883 (2011);

Larson, R. G. and Mead, D. W. The Ericksen Number and Deborah Number cascades in sheared polymeric nematics. Liq. Cryst. 15, 151-169 (1993);

Lim, S. H. and Mao, H. Q. Electrospun scaffolds for stem cell engineering. Advanced Drug Delivery Reviews 61, 1084-1096 (2009);

Lutolf, M. P., Lauer-Fields, J. L., Schmoekel, H. G., Metters, A. T., Weber, F. E., Fields, G. B., and Hubbell, J. A., Synthetic matrix metalloproteinase-sensitive hydrogels for the conduction of tissue regeneration: Engineering cell-invasion characteristics. Proc. Natl. Acad. Sci. U.S.A. 100, 5413-5418 (2003);

MacKintosh, F. C., Kas, J. and Janmey, P. A. Elasticity of semiflexible biopolymer networks. Phys Rev Lett 75, 4425-4428 (1995);

Martino, M. M., Mochizuki, M., Rothenfluh, D. A., Rempel, S. A., Hubbell, J. A., and Barker, T. H. Controlling integrin specificity and stem cell differentiation in 2D and 3D environments through regulation of fibronectin domain stability. Biomaterials 30, 1089-1097 (2009);

Nichol, J. W., Koshy, S. T., Bae, H., Hwang, C. M., Yamaniar, S., Khademhosseini, A. Cell-laden microengineered gelatin methacrylate hydrogels. Biomaterials 31, 5536-5544 (2010);

Potter, K., Balcom, B. J., Carpenter, T. A. and Hall, L. D. The gelation of sodium alginate with calcium-ions studied by magnetic-resonance-imaging (MRI). Carbohyd Res 257, 117-126 (1994);

Reneker, D. H., Yarin, A. L., Fong, H. and Koombhongse, S. Bending instability of electrically charged liquid jets of polymer solutions in electrospinning. J. Appl. Phys. 87, 4531-4547 (2000);

Seliktar, D. Designing Cell-Compatible Hydrogels for Biomedical Applications. Science 336, 1124-1128 (2012);

Shu, X. Z., Liu, Y. C., Palumbo, F. S., Lu, Y. and Prestwich, G. D. In situ crosslinkable hyaluronan hydrogels for tissue engineering. Biomaterials 25, 1339-1348 (2004);

Silva, G. A., Czeisler, C., Niece, K. L., Beniash, E., Harrington, D. A., Kessler, J. A. and Stupp, S. I., Selective differentiation of neural progenitor cells by high-epitope density nanofibers. Science 303, 1352-1355 (2004);

Williams, C. G., Kim, T. K., Taboas, A., Malik, A., Manson, P. and Elisseeff, J. In vitro chondrogenesis of bone marrow-derived mesenchymal stem cells in a photopolymerizing hydrogel. Tissue Engineering 9, 679-688 (2003);

Yang, F., Murugan, R., Wang, S, and Ramakrishna, S. Electrospinning of nano/micro scale poly(L-lactic acid) aligned fibers and their potential in neural tissue engineering. Biomaterials 26, 2603-2610 (2005);

Zhang, S. M., Greenfield, M. A., Mata, A., Palmer, L. C., Bitton, R., Mantei, J. R., Aparicio, C., Olvera de la Cruz, M., and Stupp, S. I. A self-assembly pathway to aligned monodomain gels. Nature Materials 9, 594-601 (2010); and Zong, X. H., Kim, K., Fang, D., Ran, S., Hsiao, B. S., and Chu, B. Structure and process relationship of electrospun bioabsorbable nanofiber membranes. Polymer 43, 4403-4412 (2002).

International PCT patent application publication number WO2007/066715 for "Uniaxially Oriented Hydrogel."

Kaneko, T., et al., Mechanically drawn hydrogels uniaxially orient hydroxyapatite crystals and cell extension, Chem. Mater. 5596-5601 (2004).

Matsumoto, T., et al., Three-dimensional cell and tissue patterning in a strain fibrin gel system, PLoS ONE 2(11): e1211 (2007).

Vader, D., et al., Strain-induced alignment in collagen gels, PLoS ONE 4(6): e5902 (2009).

Guo, C. and Kaufman, L. J., Flow and magnetic field induced collagen alignment, Biomaterials 28: 1105-1114 (2007).

Freyssinet, J.-M, Torbet, J., Hudry-Clergeon, G., and Maret., G., Fibrinogen and fibrin structure and fibrin formation measured by using magnetic orientation, Proc. Nad Acad. Sci. USA 80 (1983).

U.S. Pat. No. 6,057,137 for Tissue-Equivalent Rods Containing Aligned Collagen Fibrils and Schwann Cells to Tranquillo et al., issued May 2, 2000.

U.S. Patent Application Publication No. US2011/0311949 for Aligned Collagen and Method Therefor to Akkus et al., published Dec. 9, 2010.

Tonsomboon, K., and Oyen, M. L., Composite electrospun gelatin fiber-alginate gel scaffolds for mechanically robust tissue engineered cornea, J. Mechanical Behavior of Biomedical Materials, http://dx.doi.org/10.1016/j.jmbbm.2013.03.001.

U.S. Patent Application Publication No. US2008/0299657 for Aligned Nanofibers and Related Methods of Use to Stupp et al., published Dec. 4, 2008.

Yang, Y., et al., Monitoring the effect of magnetically aligned collagen scaffolds on tendon tissue engineering by PSOCT, Proc. SPIE 7179, Optics in Tissue Engineering and Regenerative Medicine III, 717903 (Feb. 12, 2009).

Freyssinet, J.-M., et al., Fibrinogen and fibrin structure and fibrin formation measured by using magnetic orientation, Proc. Natl. Acad. Sci. USA, vol. 80: 1616-1620 (1983).

Wall, B. D., et al., Aligned macroscopic domains of optoelectronic nanostructures prepared via shear-flow assembly of peptide hydrogels, Adv. Mater., 23, 5009-5014 (2011).

Zhang, S., et al., A self-assembly pathway to aligned monodomain gels, Nature Materials, vol. 9:594-601 (2010).

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for preparing a hydrogel microfiber having a uniaxial internal alignment, the method comprising:
   (a) providing at least one starting aqueous solution comprising one or more polymers;
   (b) applying an electrical potential to the at least one starting aqueous solution sufficient to initiate a jet stream of polymer solution; and
   (c) mechanically stretching the jet stream of polymer solution during or after collecting the jet stream of polymer solution in a collection bath comprising a stabilizing solution, wherein the collection bath is positioned at a separation distance between about 3 cm to about 6 cm such that the jet stream of polymer solution is collected before it is accelerated by an electrical field created by the applied electrical potential, wherein (i) the collection bath comprises a stationary collection plate, and wherein the jet stream of polymer solution is deposited on the stationary collection plate using a back and forth motion to mechanically stretch the jet stream of polymer solution as it is deposited on the stationary collection plate; or (ii) the collection bath comprises a stationary collection plate, and wherein the jet stream of polymer solution is deposited on the stationary collection plate using a back and forth motion to mechanically stretch the jet stream of polymer solution as it is deposited on the stationary collection plate.

2. The method of claim 1, wherein the one or more polymers comprise a natural polymer.

3. The method of claim 2, wherein the natural polymer is selected from the group consisting of water soluble polysaccharides, proteins, and combinations or blends thereof.

4. The method of claim 2, wherein the natural polymer is selected from the group consisting of one or more of alginate, fibrinogen, gelatin, collagen, hyaluronic acid, chitosan, chondroitin sulfate, dextran sulfate, heparin, heparan sulfate, functionalized derivatives thereof, and combinations or blends thereof.

5. The method of claim 1, wherein the one or more polymers comprise a synthetic polymer.

6. The method of claim 5, wherein the synthetic polymer is selected from the group consisting of a polyester and a polyamide.

7. The method of claim 6, wherein the polyester is selected from the group consisting of polylactic acid and poly(lactic-co-glycolic) acid.

8. The method of claim 5, wherein the synthetic polymer is selected from the group consisting of a polyacrylate, a poly(vinyl alcohol), a poly(ethylene glycol), functionalized derivatives thereof, and combinations or blends thereof.

9. The method of claim 1, wherein the at least one starting aqueous solution further comprises a thickening agent capable of increasing a viscosity of the jet stream of polymer solution.

10. The method of claim 9, wherein the thickening agent comprises polyethylene glycol (PEG).

11. The method of claim 1, further comprising crosslinking the hydrogel microfiber.

12. The method of claim 11, wherein the crosslinking, selected from the group consisting of ionic crosslinking, ultraviolet crosslinking, enzymatic crosslinking, and a chemical crosslinking reaction.

13. The method of claim 11, comprising adding a crosslinking agent to the at least one starting aqueous solution comprising one or more polymers.

14. The method of claim 11, comprising adding a crosslinking agent to the jet stream of polymer solution after the jet stream of polymer solution is initiated by the applied electrical potential.

15. The method of claim 11, comprising adding a crosslinking agent to the collection bath.

16. The method of claim 1, wherein the electrical potential has a range from about 2 kV to about 6 kV.

17. The method of claim 1, wherein the stabilizing solution comprises a solvent in which the jet stream of polymer solution is insoluble and precipitates in the stabilizing solution.

18. The method of claim 17, wherein the jet stream of polymer solution comprises an aqueous solution and one or more water-soluble polymers and the stabilizing solution comprises an organic solvent.

19. The method of claim 1, further comprising elongating the hydrogel microfiber by applying mechanical stress along the uniaxial internal alignment thereof, and drying the hydrogel microfiber.

20. The method of claim 1, further comprising combining multiple hydrogel microfibers to form a fiber bundle.

21. The method of claim 1, wherein:
(a) the at least one starting aqueous solution comprises a blend of two different polymers; or
(b) two starting aqueous solutions are provided, wherein each starting aqueous solution comprises a different polymer; and
the hydrogel microfiber comprises a bicomponent fiber having a core and a sheath.

22. The method of claim 1, further comprising adding one or more bioactive agents to the at least one starting aqueous solution.

23. The method of claim 1, further comprising depositing one or more bioactive agents on the hydrogel microfiber after it is formed.

24. The method of claim 1, further comprising adding one or more cells to the at least one starting aqueous solution.

25. The method of claim 1, further comprising seeding the hydrogel microfiber with one or more cells on a surface of the hydrogel microfiber after it is formed.

* * * * *